United States Patent [19]
Ejlersen

[11] Patent Number: 5,968,021
[45] Date of Patent: Oct. 19, 1999

[54] MAGAZINE AND REMOVABLE NEEDLE UNIT

[75] Inventor: Henning Munk Ejlersen, Vedbaek, Denmark

[73] Assignee: Novo Nordisk A/S, Bagsvaerd, Germany

[21] Appl. No.: 08/696,898

[22] PCT Filed: Feb. 27, 1995

[86] PCT No.: PCT/DK95/00085

§ 371 Date: Aug. 22, 1996

§ 102(e) Date: Aug. 22, 1996

[87] PCT Pub. No.: WO95/23005

PCT Pub. Date: Aug. 3, 1995

[30] Foreign Application Priority Data

Feb. 28, 1994 [DK] Denmark ................................. 0236/94

[51] Int. Cl.[6] .............................. A61M 5/00; B65D 83/10
[52] U.S. Cl. ......................... 604/263; 604/192; 604/240; 604/199; 206/365
[58] Field of Search ..................................... 604/263, 192, 604/232, 199, 110, 111, 194, 239, 240–243, 198, 181, 187; 128/919; 206/363–368, 438, 514

[56] References Cited

U.S. PATENT DOCUMENTS

| | | | |
|---|---|---|---|
| 3,989,044 | 11/1976 | Meierhoefer | 604/192 |
| 4,772,272 | 9/1988 | McFarland | 604/263 |
| 4,840,272 | 6/1989 | Goldman | 206/365 |
| 4,961,730 | 10/1990 | Poncy | 604/263 |
| 4,968,304 | 11/1990 | Alter et al. | 604/263 |
| 5,226,894 | 7/1993 | Haber et al. | |
| 5,312,370 | 5/1994 | Talonn et al. | 604/198 |

FOREIGN PATENT DOCUMENTS

| | | | |
|---|---|---|---|
| 1008136 | 5/1952 | France | 206/365 |
| 88/06463 | 9/1988 | WIPO . | |

Primary Examiner—Ronald K. Stright, Jr.
Attorney, Agent, or Firm—Steve T. Zelson, Esq.

[57] ABSTRACT

A needle unit comprises a needle mounted in a hub having a sleeve made from a deformable material and surrounding an end of the needle at a radial distance from that needle. The sleeve is designed to be snap-locked onto a connecting piece at the outlet end of a syringe by protrusions on the inner wall of the sleeve engaging a circumferential recess in the outer wall of the connecting piece. It is also designed such that the locking engagement between the protrusions of this sleeve and the recess of the connecting piece is released when certain zones of the outer sleeve wall are pressed inwardly. A magazine for storing the needle unit comprises a compartment which can receive the needle unit in a plurality of rotational positions. The needle unit and magazine include a syringe/needle unit release mechanism which, in a first rotational position, does not press the release zones inwardly, thereby allowing the needle unit to lock onto the syringe, but which in a second rotational position, presses the release zones inwardly so that the needle disengages from the syringe and remains inside the magazine for disposal.

15 Claims, 5 Drawing Sheets

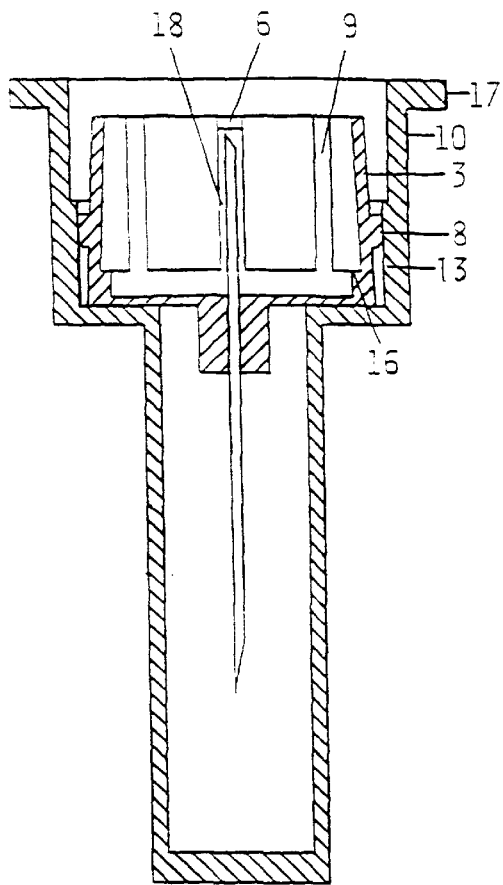
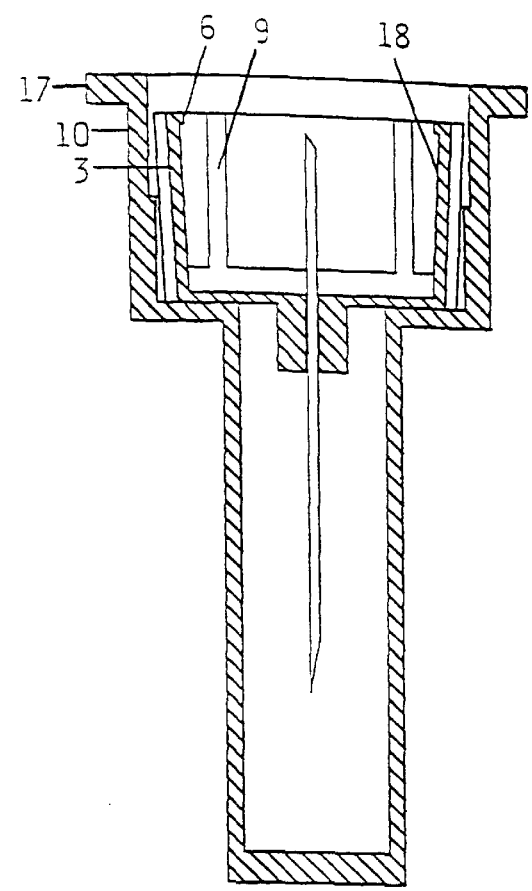
Fig. 12
Fig. 14
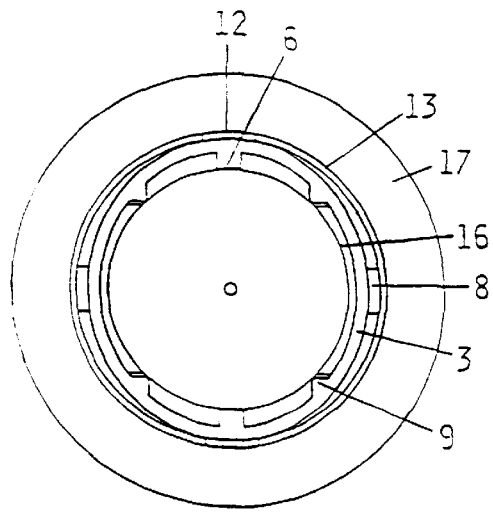
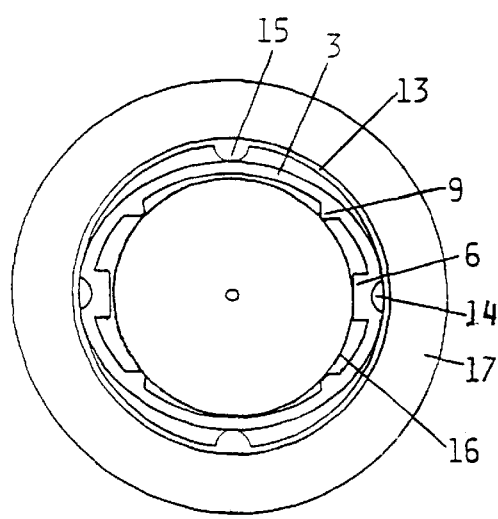
Fig. 13
Fig. 15

MAGAZINE AND REMOVABLE NEEDLE UNIT

CROSS-REFERENCE TO RELATED APPLICATIONS

This application is a 35 U.S.C. 371 national application of PCT/DK95/00085 filed Feb. 27, 1995, which is incorporated herein by reference.

BACKGROUND OF THE INVENTION

The invention relates to needle units for disposable injection needles, and specifically a needle unit comprising a needle mounted in a hub having a sleeve made from a plastic material and surrounding an end of the needle in a distance from that needle, the unit being designed to be mounted at the outlet end of a syringe having a cylindric connecting piece with a recess in a plane perpendicular to the cylinder axis, which connecting piece is received in the sleeve of the needle unit.

DESCRIPTION OF RELATED ART

By known needle units an inner surface of the depending sleeve is provided with an inner thread corresponding to an outer thread on the connecting piece of the syringe which the unit is intended for. The unit may then be mounted on the syringe simply by screwing it onto the connecting piece of the syringe.

However, such a screwing may be difficult to perform especially to people with reduced tactile motor function, and particularly unscrewing of a used unprotected sharp needle may be difficult if the screw connection has been carefully tightened when the unit was mounted.

Needle units are known of a type which can without screwing be mounted on a syringe which instead of a thread has a circumferential recess at the inner end of its connecting piece. Such needle units have at the inner side of their depending sleeves protrusions engaging the recess of the receiving connecting piece of the syringe. This construction is known from disposable syringes formed by snapping a needle unit onto the neck end of a cylinder ampoule, whereafter the syringe with the needle unit mounted is disposed of after use as a unity, as the needle unit cannot easily be demounted.

SUMMARY OF THE INVENTION

The object of the invention is to provide a needle unit of the snap-on type, which may easily be snapped onto a durable pen type syringe and which may easily be dismounted from the syringe to make it possible to change the needle without having to dispose of the syringe.

This is obtained by a needle unit of the above mentioned type, which unit is characterized in that the sleeve is so designed that the locking engagement between the protrusions of this sleeve and the recesses of the connecting piece is released when radial inward pressures are exerted on specific zones of the sleeve.

In an embodiment of the needle hub at least two protrusions may be provided on the inner surface of the sleeve, the apexes of these protrusions lying on a circle having its centre in the axis of the needle unit and having when the sleeve is not deformed a radius which is smaller than the radius of the connecting piece, and the connecting piece may fit into the sleeve with a play allowing deformation of the sleeve to an extent enlarging the radius of the circle through the apexes of the protrusions to be at least equal to the radius of the connecting piece.

The sleeve may either be deformed when the connecting piece is pressed into the sleeve urging the protrusions to pass over the side wall of this connecting piece until they snap into the recesses in this wall, or the deformation may be obtained by applying a radial inward pressures on the outer side of the sleeve at zones circumferentially displaced from the position of the protrusions. By such radial pressures the sleeve will be deformed so that the protrusions will be drawn out of the recesses in the connecting piece.

To prevent the sleeve from wriggling on the connecting piece due to the play between this sleeve and connecting piece, longitudinal spacer ribs may be provided on the inner surface of the sleeve at positions lying between the protrusions and zones lying halfway between the protrusions, which zones are designed for application of radial inward pressures.

Such spacer ribs are especially indispensable when according to the invention only two protrusions are provided diametrically opposite each other.

In another appropriate embodiment of the invention three protrusions are provided 120° circumferentially spaced. To dismount this needle unit an inward pressure may be exerted at three zones of the periphery of the sleeve, which zones must be circumferentially displaced relative to the points bearing the protrusions.

As the inward protrusions are not visible from the outer side of the sleeve, the positions of the zones for application of radial inward pressures may be indicated on the outer surface of the sleeve. The indication of the zones may appropriately be protrusions on the outer surface of the sleeve. These outward protrusions may serve further purposes as it will be described below.

The invention also concerns a magazine in which the needle unit may be stored. Such a magazine is characterized in that it comprises a compartment conforming the outer contour of the needle unit and having an access opening. The walls of this compartment may be strengthened against deformation and means for cooperation with the zones wherein radial inward pressures shall be exerted to release the hub may be provided.

The means for cooperating with the said zones may be the edge of the access opening of the magazine or of an inner strengthening of the compartment wall, which may be circular with outward recesses for accommodation of outward protrusions at the pressure zones of the sleeve when an unused needle unit is stored in the magazine, whereas engagement between the protrusions at the pressure zones of the needle unit and said edge will provide an inward pressure at said zones, when the unit is inserted in an empty magazine in a rotational position not bringing the outward protrusions on the sleeve into the outward recesses of the access opening or the strengthening of the magazine.

In another embodiment ribs may be provided on an inner cylindric wall of the compartment. In this case the sleeve must be provided with recesses in its outer cylindric wall, which recesses may accommodate said ribs when an unused needle unit is stored in the magazine. These recesses are provided in the outer wall at the positions wherein the inward protrusions of the needle hub sleeve are provided and thereby indirectly indicates the position of the pressure zones as the zones between two recesses. When a needle unit is returned to a magazine in a rotational position wherein the ribs are not accommodated in the recesses, the ribs will exert a pressure on the zones lying between these recesses and will provide the necessary deformation of the sleeve to release the engagement between the inward protrusions of the sleeve and the recesses of the connecting piece of the syringe.

The compartment wall is strengthened to be able to impart the necessary pressure to the zones without being deformed itself. This strengthening may be obtained by the access opening being surrounded by a flange. This flange and the compartment of the magazine may be one integral plastic member.

The flange may appropriately be used as the support for a foil which fixed to the flange covers the access opening and seals the compartment

BRIEF DESCRIPTION OF THE DRAWINGS

In the following a needle unit and a magazine according to the invention will be described in further details with references to the drawing, wherein FIG. 12 shows a sectional side view of a magazine with a needle unit according to FIGS. 1–3 finally deposited in the magazine, FIG. 13 shows the magazine and needle unit of FIG. 12 seen from the access opening of the magazine, FIG. 14 shows a sectional side view of a magazine with the needle unit of FIG. 6 finally deposited in this magazine, FIG. 15 shows the magazine of FIG. 14 seen from its open access end.

DESCRIPTION OF THE PREFERRED EMBODIMENTS

Figure 1:
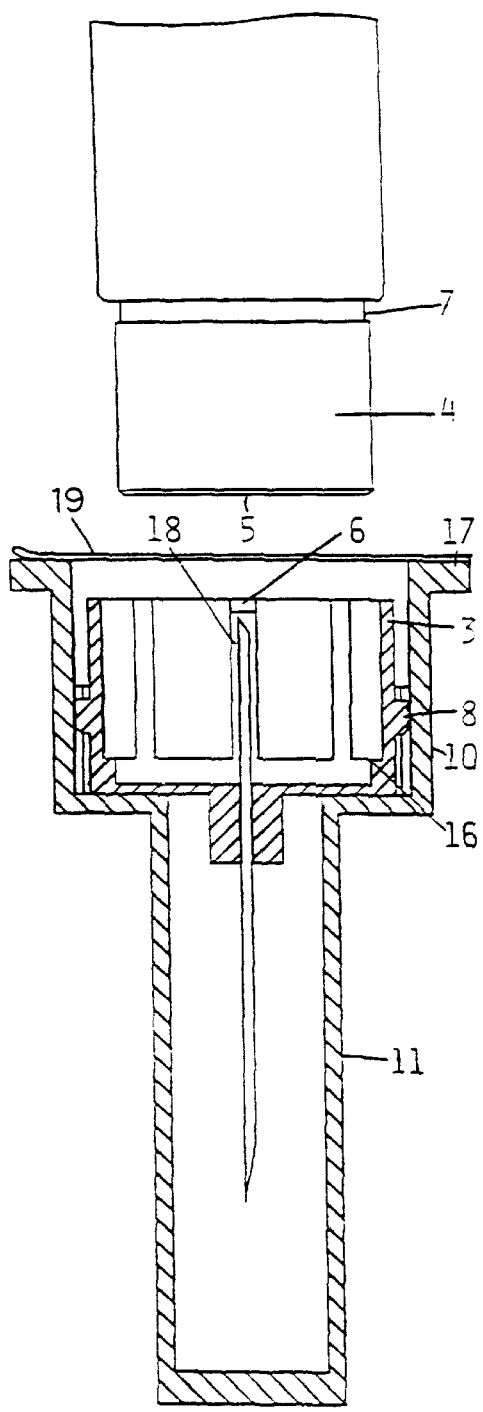
FIG. 1 shows a sectional view of a magazine with a needle unit according to the invention and a connecting piece for receiving the unit.

FIG. 1 shows a needle unit stored in a magazine. The needle unit comprises a needle 1 mounted in a needle hub 2 which has a depending sleeve 3 surrounding an end of the needle 1 in some distance from this needle. The depending sleeve 3 is designed to be received on a cylindric connecting piece 4 of a syringe so that the surrounded part of the needle penetrates a not shown rubber membrane forming at least a part of an end surface 5 of the connecting piece 4.

At two diametrically opposite positions on the inner wall of the sleeve 3 inward protrusions 6 are provided. The protrusions 6 are designed to engage a circumferential recess 7 in the connecting piece 4 receiving the needle.

Figure 2:
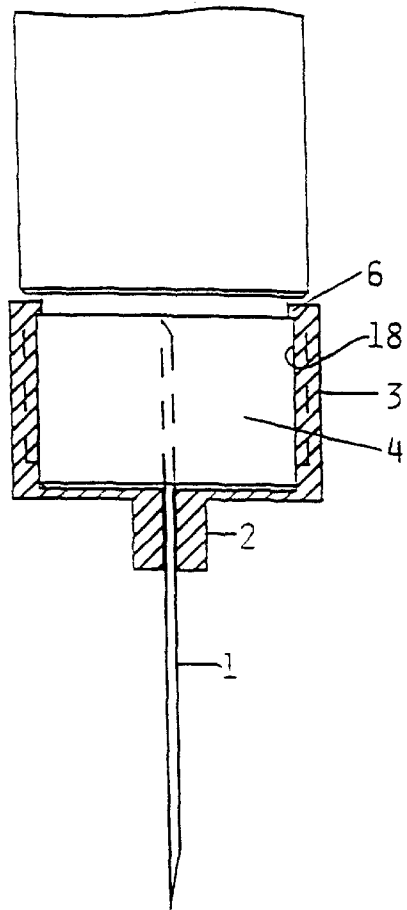
FIG. 2 shows schematically the needle unit in FIG. 1 rotated 90° and mounted on the connecting piece.

In FIG. 2 the needle unit has been rotated 90° and the receiving connecting piece 4 has been inserted into the needle unit, and it is shown how the protrusions 6 engage the recesses 7 of the connecting piece. The receiving connecting piece may be a closure part of a cylinder ampoule and the recess may be provided at the neck part of such an ampoule, but here the connecting piece is a part especially designed for cooperation with a needle unit according to the invention.

The needle hub is manufactured of a plastic material which allow some deformation of the sleeve 3 so that the diametrical distance between the apexes of the protrusions 6, which distance is smaller than the diameter of the connecting piece 4 when the sleeve is not deformed, may be increased to allow the inward protrusions 6 to pass over the side wall of the connecting piece 4 until they can snap into the recess 7 when the connecting piece 4 is pressed into the open end of the sleeve 3. During this insertion of the connecting piece 4 the open end of the sleeve 3 is deformed from having a circular appearance into an oval appearance, i.e. when the diameter connecting the inward protrusions is increased the diameter perpendicular thereto will be decreased. The not deformed sleeve must be designed to fit over the connecting piece with a play allowing this decrease.

To prevent the needle unit from wriggling due to the space between the outer wall of the connecting piece and the inner wall of the sleeve, a number of spacer ribs 9 are provide on the inner wall of the sleeve 3. These ribs will keep the connecting piece 4 centred in the sleeve 3.

Figure 3:
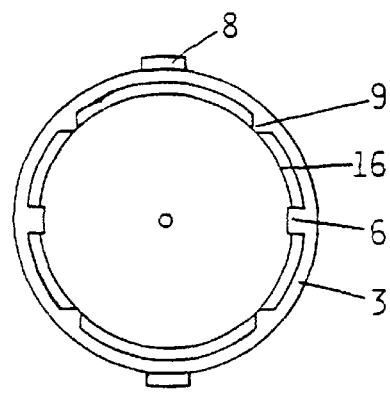
FIG. 3 shows the needle unit in FIGS. 1 and 2 seen from the open end of the sleeve.

In FIG. 3 the needle unit is seen from the open end of the sleeve. The radius of the connecting piece is indicated by a circle 16 which is formed by an edge of a guide at the inner end of the sleeve, into which guide the end of the connecting piece fits. Axial spacer ribs 9 are provided on the inner wall of the sleeve at both sides of the inward protrusions 6 but leaving the zones 90° displaced from the inward protrusions free to be pressed axially inwards until it contacts the wall of the connection piece. As indicated in FIG. 2, ribs 18 are also provided extending longitudinally in the sleeve from the inward protrusions to said guide at the inner end of the sleeve. During the exertion of the radial pressure at the said zones the spacer ribs 9 abut the connecting piece and act as fulcrums assisting the lifting of the inward protrusions 6 out of engagement with the recess 7 of the connecting piece.

When it is wanted to dismount the needle unit from the connecting piece, radial inward pressures may by two fingers be imparted on the outer side of the sleeve at said zones to disconnect the snap engagement between the inward protrusions 6 and the recess 7 of the connecting piece. Therefore it is necessary that marks on he outer side of the sleeve indicate the position of such zones or indicate the positions of the inward protrusions.

In the embodiment shown in the FIGS. 1–3 such marks are provided as outward protrusions 8 on the outer wall of the sleeve 3. These protrusions have another function which will be described below.

Figure 4:
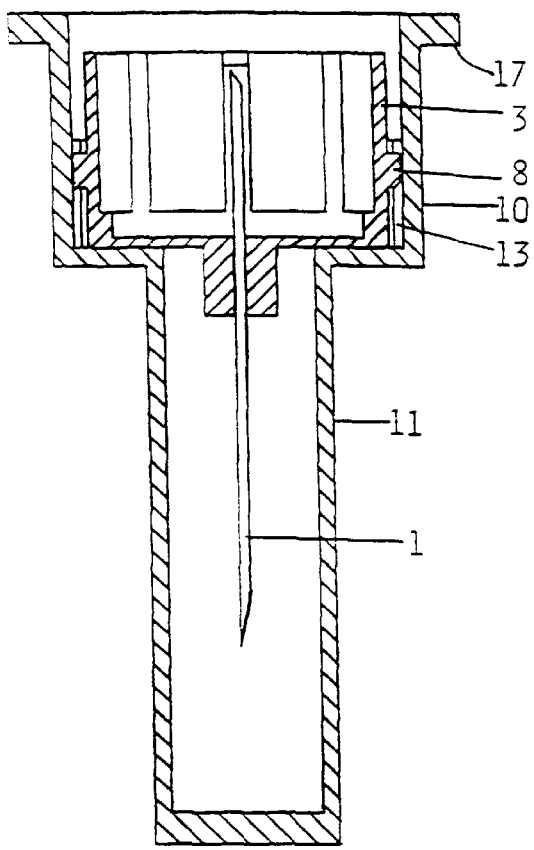
FIG. 4 shows a sectional side view of the needle unit of FIGS. 1 to 3 stored in a magazine.
Figure 5:
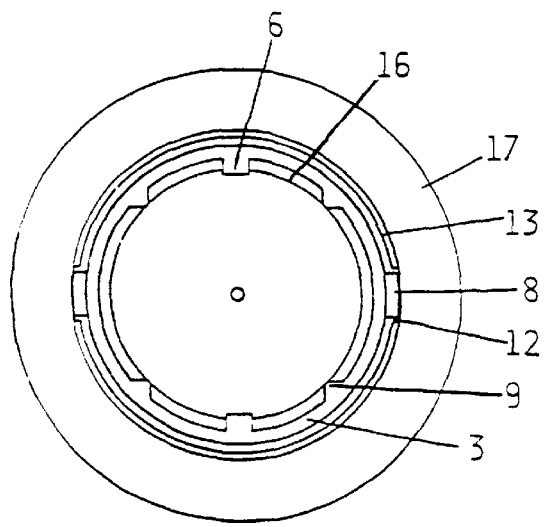
FIG. 5 shows the magazine with the stored needle unit of FIG. 4 seen from the access end of the magazine.

When a new and unused the needle unit is stored in a magazine as shown in FIGS. 4 and 5, the hub with its sleeve is supported in a compartment 10 into which it fits with a play allowing the necessary deformation of the sleeve 3. The inner space of the compartment conforms the outer contour of the hub 2, i.e. longitudinal recesses are provided in the inner wall of the compartment to accommodate the outward protrusions 8 on the sleeve 3. The needle is protected by a needle cap 11 integral with the compartment 10.

To mount a new needle unit on a syringe, the user may grasp the magazine with the unit with one hand without any risk of scratching himself by the needle. With his other hand he may grasp the syringe and insert the connecting piece of this syringe into the open end of the sleeve, the open end of which faces an open access end of the compartment of the magazine. The connection piece 4 is now pressed into the sleeve until the inward protrusions 6 of this sleeve snap into the recess 7 of this connection piece. The needle unit may now be drawn out of the magazine by the syringe.

When a used needle unit shall be disposed of, this needle unit mounted on the syringe is reinserted in the magazine but in a rotational position wherein the outward protrusions 8 of the sleeve 3 are not accommodated in the recesses 12. Thereby the outward protrusions 8 will abut a reinforcement 13 in the compartment and will be pressed radially inwards. As the outward protrusions of the sleeve are provided at the zones at which a radially inward pressure will deform the sleeve in a way bringing the inward protrusions of this sleeve out of engagement with the recesses of the connection piece, the needle unit will be disconnected from the syringe. As the outward protrusions of the sleeve are pressed into the reinforced part of the compartment, the unit will be wedged in this part and will not follow the syringe when it is retracted. A remounting of the needle unit is not possible as the sleeve remains in a deformed condition so that the inward protrusion of the sleeve will not engage the recesses of the connecting part if this part is reinserted in the sleeve. FIGS. 12 and 13 shows the described needle unit wedged into the magazine for final deposition.

To ensure that the sleeve 3 and not the compartment 10 is deformed, when the used needle unit is wedged into this compartment, the compartment wall is reinforced by the provision of the part 13 having an enlarged wall thickness. As another reinforcing feature helping the compartment 10 to keep its cylindric shape, a flange 17 is provided surrounding the access opening of the compartment. The flange 17 may further act as a support for a closure. This closure may be a foil 19 sealed along the flange 17 to enable a sterile storage of the unused needle unit.

Figure 6:
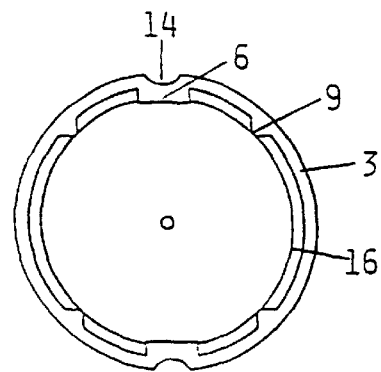
FIG. 6 shows another embodiment of a needle unit seen from the open end of the sleeve.
Figure 7:
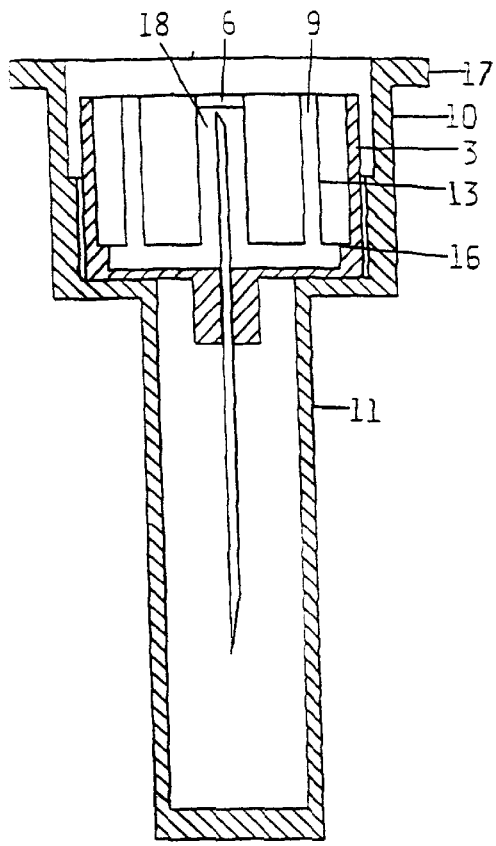
FIG. 7 shows a sectional side view of the needle unit of FIG. 6 stored in a magazine.
Figure 8:
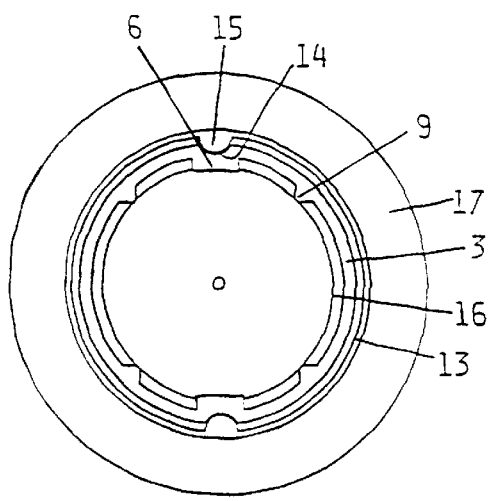
FIG. 8 shows the magazine of FIG. 7 with the stored unit seen from the open end of the magazine.

FIG. 6 shows another embodiment of a needle unit seen from the open end of the sleeve. This embodiment differs from the one shown in FIG. 6 by the positions of the inward protrusions 6 being indicated by longitudinal grooves 14 in the outer surface of the sleeve 3. FIGS. 7 and 8 shows this unit stored in a magazine having a compartment 10, a needle cap 11, and a flange 17 as has the magazine of FIGS. 4 and 5. The recesses 12 of the magazine of FIGS. 4 and 5 are in FIGS. 7 and 8 replaced by longitudinal ribs 15 which are accommodated in the grooves 14 of the needle unit when this needle unit is new and stored in the magazine. When a used needle unit is reinserted in the magazine it shall be rotated with its grooves 14 displaced 90° from the ribs 15 of the compartment. The ribs 15 will then exert the radial inward pressures on the sleeve 3 which are necessary to disengage the inward protrusions 6 of this sleeve from the recess 7 of the connecting piece. FIGS. 14 and 15 shows a needle unit of the kind just described wedged into its magazine for final deposition.

It shall be noticed that by embodiments wherein the inward pressures are provided by ribs in the compartment, the used needle unit must be reinserted into the compartment in a rotational position by which it is ensured that the ribs acts at the zones designed for being the objects of radially inward pressures. In embodiments using outward protrusions on the sleeve of the needle unit it is inherently ensured that pressures exerted by the protrusions abutting elements in the compartment are exerted at the zones carrying the outward protrusions. The only demand as to the rotational position when reinserted is that this position must differ from the position of the original storage with the outward protrusions accommodated in recesses.

Elements of the FIGS. 6, 7, and 8 which corresponds to the elements of the embodiment described in FIGS. 1–5 are given the same reference numerals.

Figure 9:
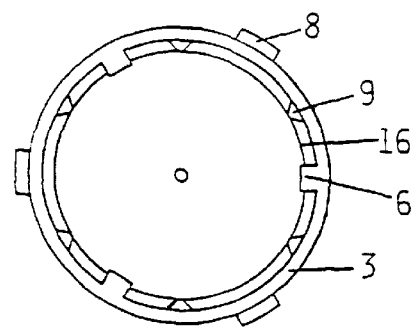
FIG. 9 shows still another embodiment of a needle unit seen from the open end of the sleeve.
Figure 10:
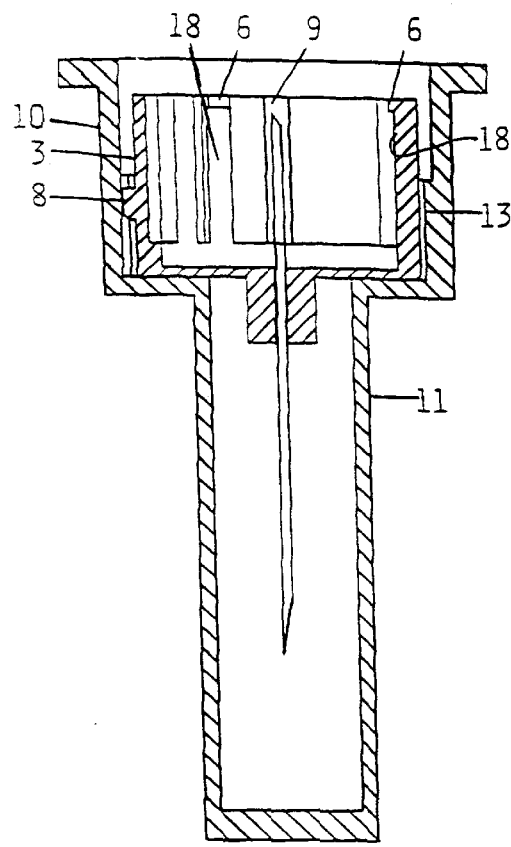
FIG. 10 shows a sectional side view of the needle unit of FIG. 9 stored in a magazine.
Figure 11:
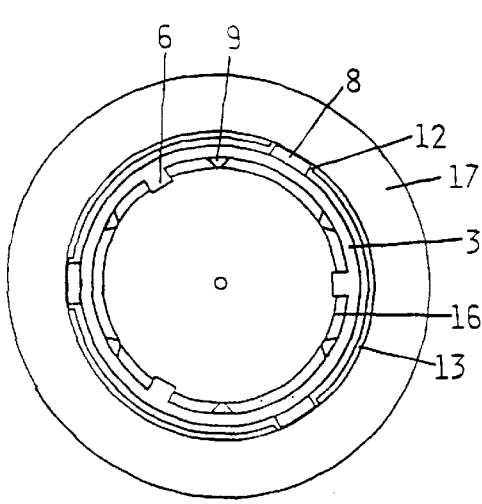
FIG. 11 shows the magazine of FIG. 10 with the stored needle unit seen from the open end of the magazine.

FIGS. 9, 10, and 11 shows still another embodiment for a needle unit and the magazine for its storage and final deposition wherein three inward protrusions 6 are provided on the sleeve 3 at 120° intervals along the inner periphery thereof. Outward protrusions 8 are provided at the zones where radially inward pressures must be exerted to release the snap engagement between the needle unit and a syringe. Spacer ribs 9 are provided in pairs at both sides of each inward protrusion leaving zones for exertion of radially inward pressures to deform the sleeve. The compartment of the magazine for storage of the new needle unit has three recesses for accommodating the outward protrusions 8 of the needle unit.

Figure 16:
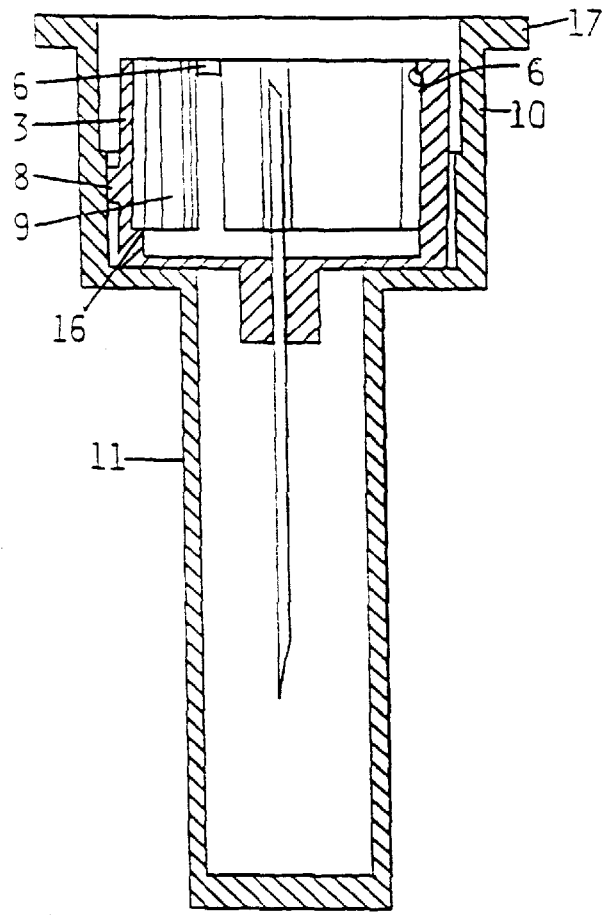
FIG. 16 shows a sectional side view of a magazine with the needle unit of FIG. 9 finally deposited in this magazine.
Figure 17:
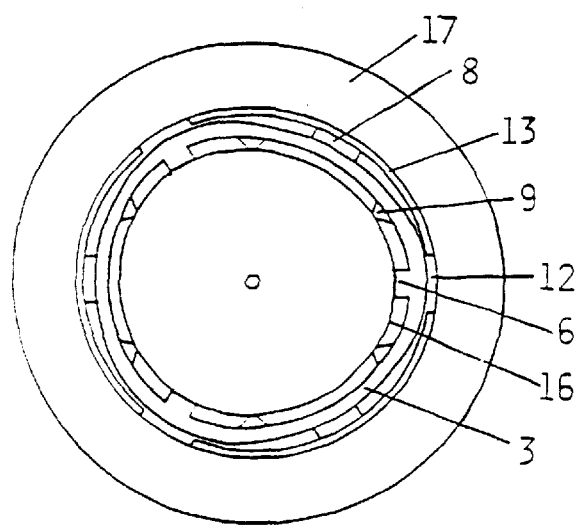
FIG. 17 shows the magazine of FIG. 16 seen from its open access end.

In FIGS. 16 and 17 it is shown how a used needle unit of this kind is wedged into the magazine for final deposition.

It appears that the needle unit will always be either mounted on a syringe or stored or disposed of in a magazine.

I claim:

1. In combination a magazine and a removable needle unit,
   wherein said needle unit comprises a needle mounted in a hub and a sleeve made from a deformable material surrounding an end of the needle at a distance from said needle, said sleeve including at least one snap-lock element designed to engage a cooperating element on the outlet end of a syringe for securing said needle unit on the syringe, and wherein said sleeve includes specific zones, spaced from said at least one snap-lock member, which when pressed radially inwardly deform said sleeve in a manner such that the locking engagement between said sleeve and the syringe outlet end is released; and
   wherein said magazine comprises a compartment for accommodating said needle unit in a plurality of rotational positions; and wherein said needle unit and magazine further include a syringe/needle unit release means which does not press said zones radially inwardly in a first rotational position of said needle unit, such that the needle unit may lock onto a syringe outlet end, and which presses said zones radially inwardly in a second rotational position of said needle unit, thereby causing said needle unit to release from a syringe outlet end.

2. A magazine and needle unit according to claim 1, wherein said syringe/needle unit release means comprises protrusions provided on the needle hub at said zones and a reinforcement part in said magazine which engages said protrusions in said second rotational position to press said zones inwardly, and which includes recesses to receive said protrusions in said first rotational position so as not to press said zones inwardly.

3. A magazine and needle unit according to claim 2, wherein said compartment has an access opening and is reinforced against deformation by a flange surrounding said opening.

4. A magazine and needle unit according to claim 3, wherein said flange and said compartment are one integral plastic member.

5. A magazine and needle unit according to claim 4, further comprising a removable foil fixed to the flange surrounding said opening for sealing said compartment.

6. A magazine and needle unit according to claim 3, further comprising a removable foil fixed to the flange surrounding said opening for sealing said compartment.

7. A magazine and needle unit according to claim 1, wherein said syringe/needle unit release means comprises a plurality of axial ribs on an inner wall of said magazine which press said specific zones inwardly in said second rotational position, and wherein said sleeve includes a plurality of axial recesses for receiving said ribs in said first rotational position so as not to press said zones inwardly.

8. A magazine and needle unit according to claim 7, wherein said compartment has an access opening and is reinforced against deformation by a flange surrounding said opening.

9. A magazine and needle unit according to claim 8, wherein said flange and said compartment are one integral plastic member.

10. A magazine and needle unit according to claim 9, further comprising a removable foil fixed to the flange surrounding said opening for sealing said compartment.

11. A magazine and needle unit according to claim 8, further comprising a removable foil fixed to the flange surrounding said opening for sealing said compartment.

12. A magazine and needle unit according to claim 1, wherein said compartment has an access opening and is reinforced against deformation by a flange surrounding said opening.

13. A magazine and needle unit according to claim 12, wherein said flange and said compartment are one integral plastic member.

14. A magazine and needle unit according to claim 13, further comprising a removable foil fixed to the flange surrounding said opening for sealing said compartment.

15. A magazine and needle unit according to claim 12, further comprising a removable foil fixed to the flange surrounding said opening for sealing said compartment.

\* \* \* \* \*